US006217574B1

(12) United States Patent
Webster

(10) Patent No.: US 6,217,574 B1
(45) Date of Patent: *Apr. 17, 2001

(54) SYSTEM AND METHOD FOR MEASURING SUBSURFACE TEMPERATURE OF TISSUE DURING ABLATION

(75) Inventor: Wilton W. Webster, Diamond Bar, CA (US)

(73) Assignee: Cordis Webster, Diamond Bar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/234,365

(22) Filed: Jan. 20, 1999

Related U.S. Application Data

(62) Division of application No. 09/205,625, filed on Dec. 3, 1998.

(51) Int. Cl.[7] .................................................. A61B 18/14
(52) U.S. Cl. .............................. 606/41; 606/34; 607/99; 607/105; 607/113
(58) Field of Search ................................. 606/41, 34, 49; 607/99, 105, 113

(56) References Cited

U.S. PATENT DOCUMENTS

| | | | |
|---|---|---|---|
| 3,920,021 | 11/1975 | Hiltebrandt | 128/303.17 |
| 4,848,352 | 7/1989 | Pohndorf et al. | 128/642 |
| 4,960,134 | 10/1990 | WEbster, Jr. | 128/786 |
| 5,334,193 | * 8/1994 | Nardella | 606/41 |
| 5,341,807 | * 8/1994 | Nardella | 128/642 |
| 5,348,554 | * 9/1994 | Imran et al. | 606/41 |
| 5,383,852 | 1/1995 | Stevens-Wright | 604/95 |
| 5,398,683 | 3/1995 | Edwards et al. | 128/642 |
| 5,462,545 | * 10/1995 | Wang et al. | 606/41 |
| 5,485,849 | 1/1996 | Panescu et al. | 128/699 |
| 5,500,012 | 3/1996 | Brucker et al. | 607/122 |
| 5,549,108 | 8/1996 | Edwards et al. | 128/642 |
| 5,673,704 | * 10/1997 | Marchlinski et al. | 607/99 |
| 5,718,701 | * 2/1998 | Shai et al. | 606/41 |
| 5,741,214 | * 4/1998 | Ouchi et al. | 600/374 |
| 5,836,990 | * 11/1998 | Li | 607/28 |
| 5,957,922 | * 9/1999 | Imran | 606/41 |
| 6,030,379 | * 2/2000 | Panescu et al. | 606/34 |

FOREIGN PATENT DOCUMENTS 0571797 12/1983 (EP) .

OTHER PUBLICATIONS

Boaz Avitall et al., "The Effects of Electrode–Tissue Contact on Radiofrequency Lesion Generation", PACE, vol. 20, Dec. 1997, Part 1, pp. 2899–2909.

(List continued on next page.)

Primary Examiner—Lee Cohen
(74) Attorney, Agent, or Firm—Christie, Parker & Hale, LLP

(57) ABSTRACT

An RF ablation system comprises irrigated split tip electrode catheter, an RF generator and a signal processor. The catheter comprises four orthogonally arranged electrodes at the distal tip. The catheter is used to map the electrical activity of a heart chamber to locate site(s) of aberrant electrical pathways to be ablated. Once an ablation site has been located, the signal processor activates the RF generator to transmit a low level RF current to each electrode member of the split tip electrode. The signal processor receives signals indicative of the impedance between each electrode member and one or more surface indifferent electrodes and determines which electrode members are associated with the highest impedance. Such electrode members are those in greatest contact with the myocardium. The signal processor then automatically activates the RF generator to transmit an RF ablation current to the electrode members in contact with the myocardium to create a lesion.

30 Claims, 8 Drawing Sheets

OTHER PUBLICATIONS

Hiroshi Nakagawa M.D., Ph.D. et al., "Comparison of In Vivo Tissue Temperature Profile and Lesion Geometry for Radiofrequency Ablation With a Saline–Irrigated Electrode Versus Temperature Control in a Canine Thigh Muscle Preparation", Circulation, American Heart Association, Inc., vol. 91, No. 8, Apr. 15, 1995, pp. 2264–2273.

Hiroshi Nakagawa M.D., Ph.D. et al., "Inverse Relationship Between Electrode Size and Lesion Size During Radiofrequency Ablation With Action Electrode Cooling", Circulation, American Heart Association, Inc., vol. 98, Aug. 4, 1998, pp. 458–465.

* cited by examiner

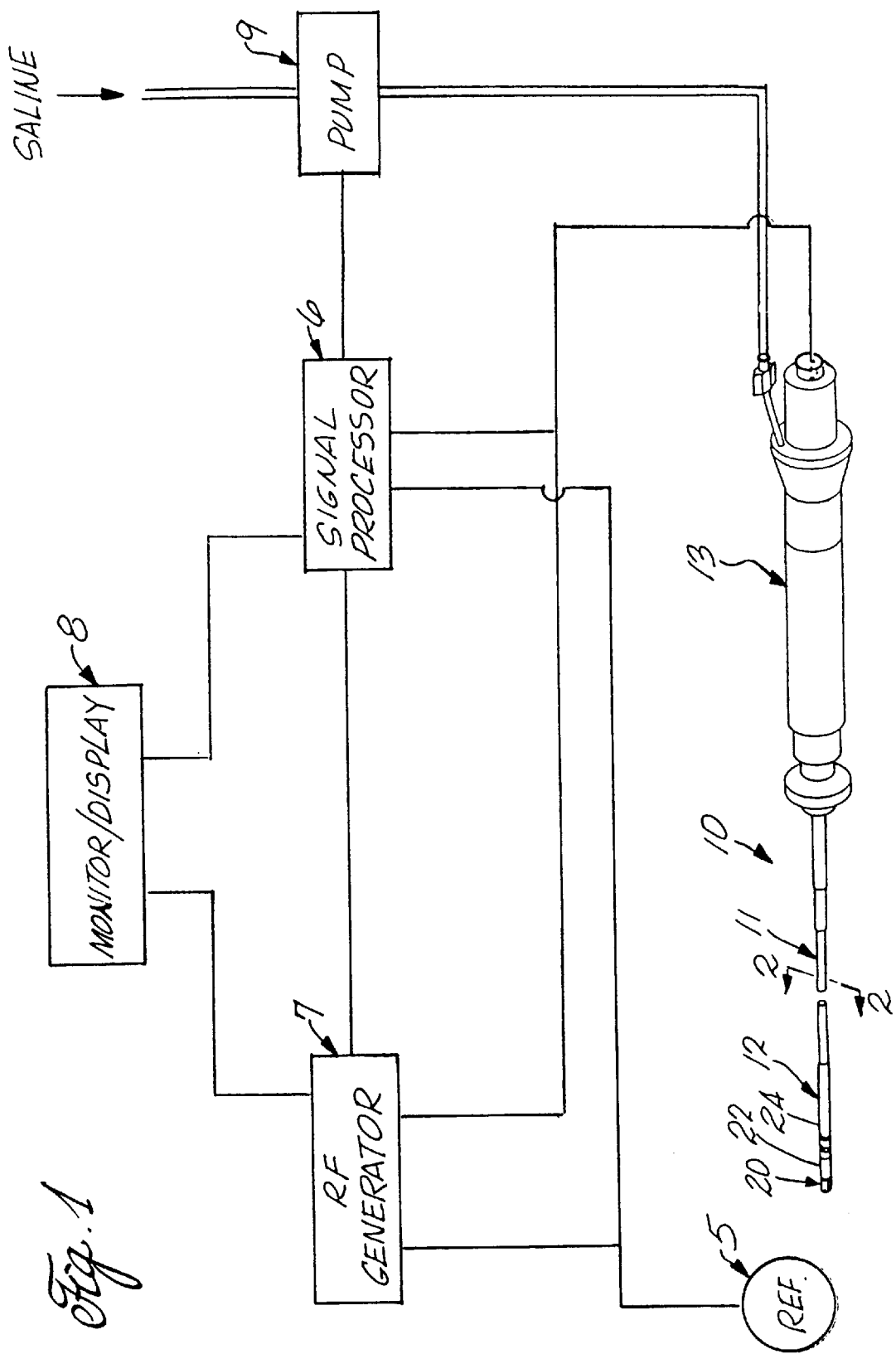

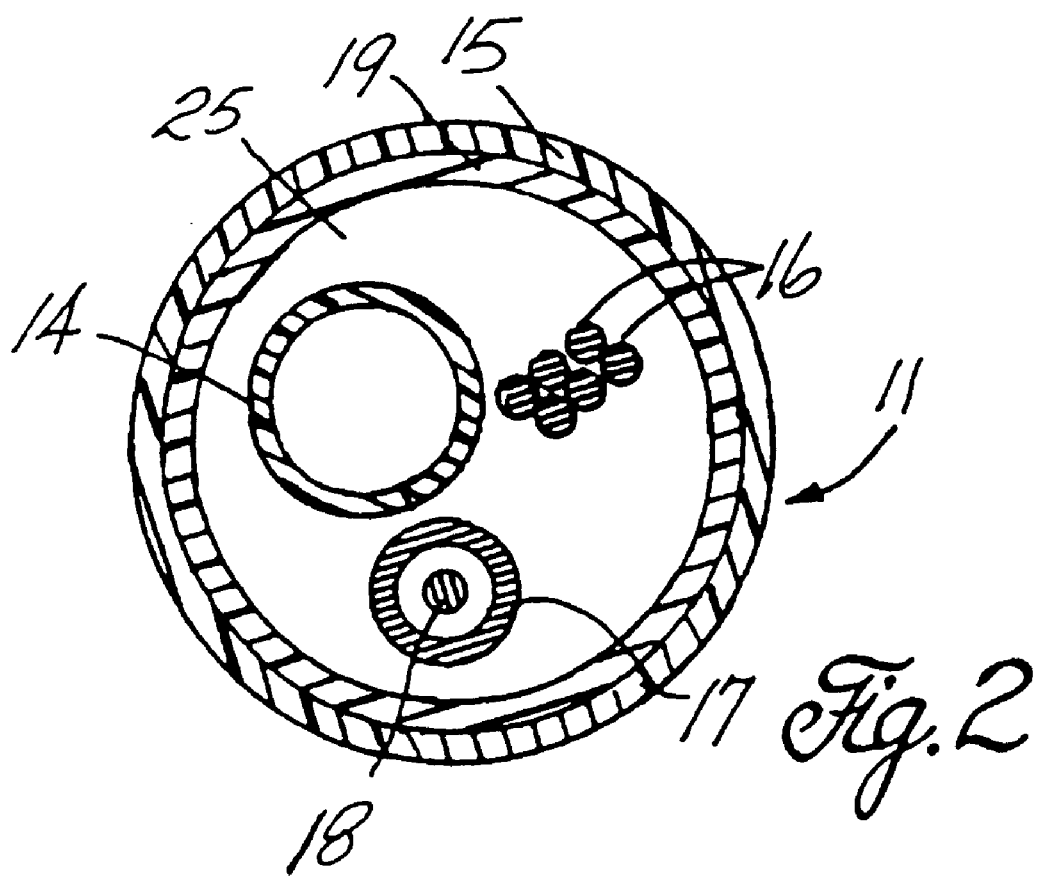

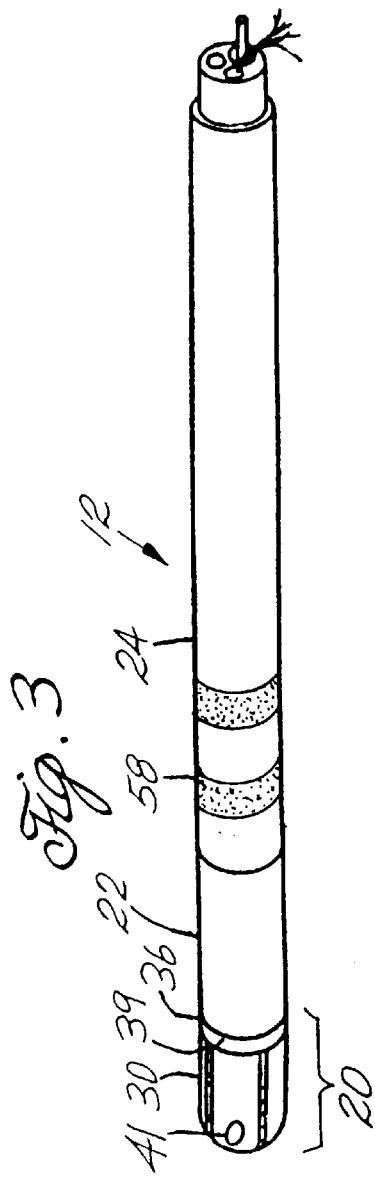
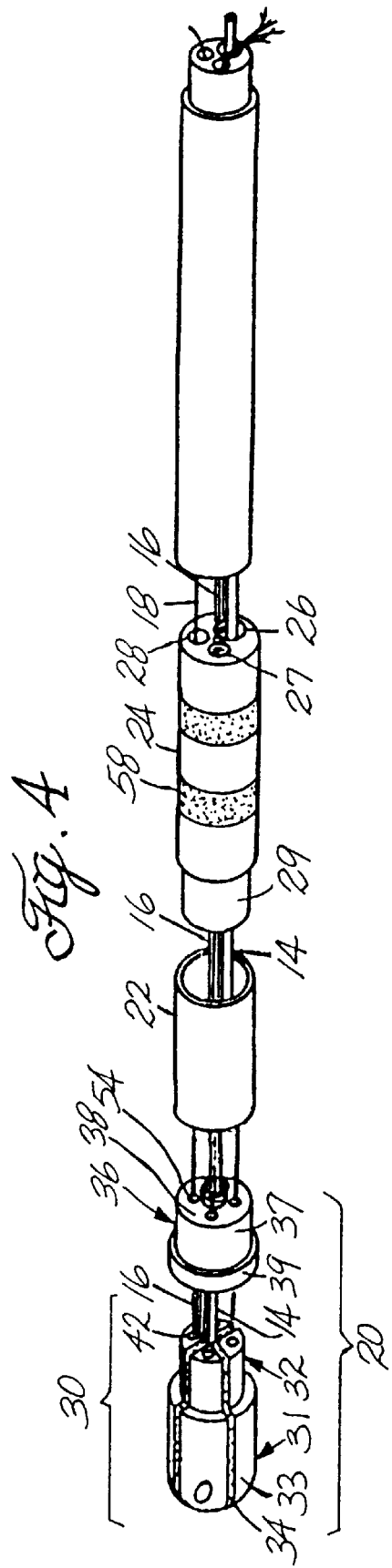

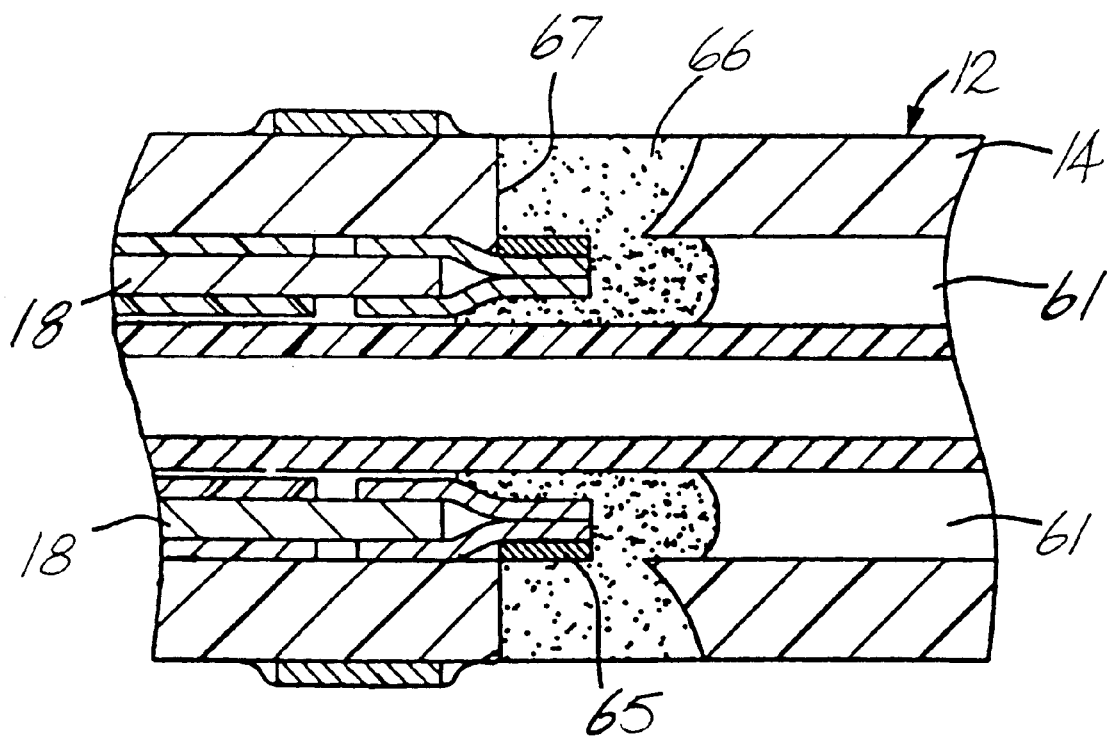

SYSTEM AND METHOD FOR MEASURING SUBSURFACE TEMPERATURE OF TISSUE DURING ABLATION

CROSS-REFERENCE TO RELATED APPLICATION

This application is a divisional of U.S. Pat. application No. 09/205,628, filed Dec. 3, 1998.

FIELD OF THE INVENTION

This invention relates to an electrophysiology catheter system having a split tip electrode catheter and a signal processing system for providing a safe and effective RF ablation of the heart tissue.

BACKGROUND OF THE INVENTION

The heart has a natural pacemaker and conduction system which causes the heart muscle to contract, or beat, in an orderly rhythmical manner. The normal pacing rate for an adult at rest is about 60 to 70 beats per minute. There are many physiologic abnormalities which cause one or more chambers of the heart to beat more rapidly (tachycardia or flutter) or chaotically (fibrillation). A patient cannot live with ventricular fibrillation because there would be no blood pumped through the arteries, but may live with atrial fibrillation so long as the chaotic impulses are filtered out at the AV node and do not reach the ventricals. A patient may also live with atrial flutter and various forms of tachycardia but quality of life may be considerably compromised.

Many of these arrhythmias can be treated effectively by ablation using radio-frequency (RF) energy. Other arrhythmias are less effectively treated, requiring more RF lesions for a successful outcome or resulting in no successful outcome. RF ablation is performed with a catheter having one or more electrodes which deliver the RF energy to the cardiac tissue. In operation the catheter is guided through a vein or artery into the heart chamber and positioned at one or more sites, determined by an electrophysiologist, to correct the arrhythmia. The catheter delivers energy from an external source (generator) to the tissue, generating sufficient heat to kill the tissue, which is thereafter replaced by scar tissue. In a successful ablation procedure, the lesions formed interrupt the electrical pathways that cause the arrhythmia so that heart rhythm is improved or returns to normal.

During ablation, it is important to control the temperature of the tissue, both at the tissue surface and below. If the surface temperature becomes excessive, dehydration and charring. results. Charred tissue presents a dangerous situation as it may flake off resulting in blockage of a blood vessel. Excessive heating below the surface is also dangerous as it may result in a "steam pop." A "steam pop" occurs when deep tissue is heated to a temperature sufficient to boil the water of the tissue which creates a steam bubble within the tissue. Such a steam bubble erupts through the surface of the myocardium with substantial force. This eruption can typically be heard as a "pop" by the electrocardiologist.

SUMMARY OF THE INVENTION

The present invention provides an improved system and method for ablating myocardial tissue. The system comprises an electrophysiology catheter having a split tip electrode at its distal end. The split tip electrode preferably comprises a tip electrode assembly having two or more orthogonally arranged electrode members. In a preferred embodiment, there are five electrode members which comprise the split tip electrode. The electrode members are arranged so that four of the members form sectors of a hemisphere and the fifth forms a ring behind the four member hemisphere. The split tip electrode catheter preferably comprises means for passing a fluid, e.g., saline, through each of the electrode members for cooling the electrode members during ablation. A particularly preferred irrigated split tip electrode is disclosed in patent application entitled IRRIGATED SPLIT TIP ELECTRODE CATHETER to Webster, Jr. (U.S. application No. 09/205,116) which is filed concurrently herewith and incorporated herein by reference.

The system further comprises means, electrically connected to each of the electrode members of the split tip electrode, for receiving electrical signals from each of the electrode members and for generating a record and/or display indicative of those signals, preferably an electrogram.

Also electrically connected to each of the electrode members of the split tip electrode is a means for measuring the electrical impedance between each electrode member and a reference electrode to determine which of the electrode members are in contact with the myocardium. The impedance measuring means comprises an RF generator for generating a low level RF electrical signal, preferably about 2 microamperes at a frequency of about 50 KHz, means for delivering the low level RF current to each of the electrode members, at least one reference or indifferent electrode, e.g., a skin patch electrode, and preferably means for generating a record and/or display of the impedance between each electrode member and the reference electrode(s).

Means are also provided for delivering an ablating RF current to one or more of the electrode members of the split tip electrode for ablating myocardial tissue in contact with those electrode members. Such means comprises an RF generator for generating RF current sufficiently strong to ablate heart tissue. Preferred ablating currents are from about 0.25 to about 1.0 amperes at about 400 KHz to about 700 KHz, more preferably about 0.5 to 0.75 amperes at 500 KHz. A signal processor is provided for activating the RF generator to transmit the low level RF current to each of the electrode members of the split tip electrode and for comparing the impedances associated with each electrode member of the split tip electrode to determine which electrode member(s) is (are) associated with the highest impedance. This allows the identification of the electrode members in contact with the myocardium as those electrode members will be associated with a higher impedance than those electrode members in contact only with the blood pool. The signal processor also activates the RF generator to selectively transmit RF ablation current to only those electrode members in contact with the myocardium.

It is preferred that the system comprise an irrigated split tip electrode catheter and a metering pump for pumping a cooling fluid through the catheter to cool the ablating electrode(s) during ablation. In such an embodiment, it is also preferred that the signal processor be capable of activating the pump and the RF generator intermittently so that there are periods of no irrigation and RF ablation energy between periods wherein RF ablation energy and cooling fluid are delivered to the ablation electrodes.

In a preferred embodiment of the invention, the ablation system further comprises an irrigated split tip electrode catheter and means for monitoring the surface and/or subsurface and temperatures of the tissue being ablated. Preferred surface temperature monitoring means comprises a thermocouple or thermistor coupled to each electrode member of the split tip electrode for generating an electrical signal indicative of the temperature of the electrode members in contact with the myocardium and signal processor intermittently activating and deactivating the RF ablation current generator and the irrigation pump. During the deactivated periods, the electrode temperature reaches the approximate surface temperature of the tissue being ablated and is therefore an estimate of the tissue temperature at the tissue-electrode interface. Preferred sub-surface temperature monitoring means comprises impedance monitoring means for monitoring the impedance associated with the electrode members of the split tip electrode, and estimating the maximum deep tissue temperature from the impedance measurements. Preferably, means are also provided for automatically reducing the amount of RF current delivered to the selected electrode members when the temperature and/or impedance reaches pre-determined levels to prevent excessive surface or deep tissue temperature rise.

BRIEF DESCRIPTION OF THE DRAWINGS

FIG. 1 is a schematic diagram showing preferred irrigated split tip electrode catheter and signal processing RF ablation system.

FIG. 2 is a transverse cross-sectional view of the catheter body along line 2—2 in FIG. 1.

FIG. 3 is a perspective view of the tip section of the preferred irrigated split tip electrode catheter of FIG. 1.

FIG. 4 is an exploded perspective view of the tip section of the preferred irrigated split tip electrode of FIG. 1.

FIG. 8A is a longitudinal cross-sectional view of a portion of the tip section of FIG. 8 showing a preferred means for anchoring puller wires to the side wall of the tubing of the tip section.

DETAILED DESCRIPTION OF THE INVENTION

Figure 5:
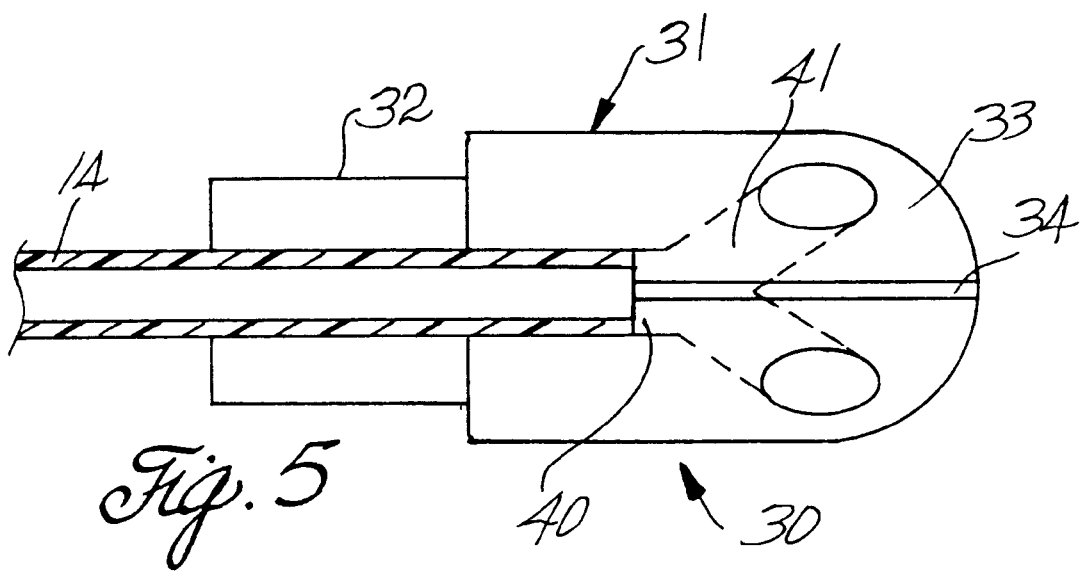
FIG. 5 is a side view of the split tip electrode of the catheter of FIG. 1.

With reference to FIG. 1, there is shown a schematic diagram of a preferred system for mapping electrical signals in the heart to locate aberrant electrical pathways and to ablate heart tissue to interrupt such aberrant electrical pathways. The system comprises a split tip electrode catheter 10, preferably an irrigated split tip electrode catheter, as shown, one or more reference or indifferent electrodes 5, a signal processor 6, an RF current generating unit 7, a monitor 8 and or display, and a pump 9 for pumping a fluid into and through an infusion tube in the catheter.

The catheter 10 comprises an elongated catheter body 11 and a tip section 12 at the distal end of the catheter body 11 and a control handle 13 at the proximal end of the catheter body 11. The catheter body 11 comprises an elongated tubular construction having a single, central or axial lumen 25. The catheter body 11 is flexible, i.e., bendable, but substantially non-compressible along its length. The catheter body 11 can be of any suitable construction and made of any suitable material. A presently preferred construction comprises an outer wall 15 made of a polyurethane or the like and an inner stiffening tube 19. The outer wall comprises an imbedded braided mesh of stainless steel or the like to increase torsional stiffness of the catheter body 11 so that, when the control handle 13 is rotated, the tip section of the catheter 10 will rotate in a corresponding manner. The outer diameter of the catheter body 11 is not critical, but is preferably no more than about 8 french. Likewise the thickness of the outer wall is not critical.

The inner surface of the outer wall is lined with a stiffening tube 19, which can be made of any suitable material, preferably polyimide. The stiffening tube 19, along with the braided outer wall 15, provides improved torsional stability while at the same time minimizing the wall thickness of the catheter, thus maximizing the diameter of the single lumen. The outer diameter of the stiffening tube 19 is about the same as or slightly smaller than the inner diameter of the outer wall. Polyimide tubing is presently preferred because it may be very thin walled while still providing very good stiffness. This maximizes the diameter of the central lumen without sacrificing strength and stiffness.

A particularly preferred catheter body 11 has an outer wall with an outer diameter of about 0.092 inch and an inner diameter of about 0.063 inch and a polyimide stiffening tube having an outer diameter of about 0.061 inch and an inner diameter of about 0.052 inch.

As shown in FIG. 2, extending through the lumen are an infusion tube 14, a plurality of electrode lead wires 16, having an insulation coating, and a compression coil 17 in surrounding relation to a puller wire 18.

An enlarged side view of the tip section 12 is shown in FIGS. 3 and 4. The tip section comprises a split tip electrode 20 comprising a "quad" tip electrode, i.e. a four member tip electrode assembly 30 and a cup electrode 36. The tip section 12 further comprises a bridge tubing 22 and a section of flexible tubing 24. The tubing 24 is made of a suitable non-toxic material which is preferably more flexible than the catheter body 11. A presently preferred material for the tubing 24 is braided polyurethane, i.e., polyurethane with an embedded mesh of braided stainless steel or the like. The outer diameter of the tip section 12, like that of the catheter body 11, is preferably no greater than about 8 french. The proximal end of the flexible tubing 24 is attached to the distal end of the catheter body 11 by any suitable means.

In the embodiment shown, the flexible tubing 24 has three off axis lumens, a first lumen 26 through which the infusion tube 14 extends, a second lumen 27 through which the electrode lead wires 16 extend and a third lumen 28 through which the puller wire 18 extends. The diameter of the three lumens may be the same or may differ a desired. The presently preferred diameters of the first, second and third lumens are about 0.035 inch, about 0.022 inch and about 0.022 inch. The length of the flexible tubing is not critical but is preferably about 2 to 3 inches. The distal end of the flexible tubing is recessed or stepped down to form a distal stem 29 which fits into the proximal end of the bridge tubing 22.

With reference to FIG. 4, the quad tip electrode 30 has a distal portion 31 having an exterior surface with a preferably rounded or bullet shaped distal end, and a proximal portion 32 which forms a recessed stem. The outer diameter of the distal portion 31 is preferably 8 french or less. The overall length of the distal portion is not critical but is sufficient for ablation. A presently preferred length is about 2.5 mm.

The quad tip electrode 30 comprises four electrode members 33. Each electrode member 33 comprises a pair of flat interior surfaces and an exterior surface. The electrode members 33 are arranged with each flat side of each electrode member adjacent to a flat side of another electrode member, separated therefrom by insulation 34, preferably high-temperature epoxy. To facilitate the connection of electrode and lead wires 16, each electrode member 33 further comprises an electrode lead bore 42 in its proximal end generally parallel to the axis of the catheter body 11.

Each of the electrode members 33 can be of any suitable construction and is preferably made of platinum. It is understood that the number, shape and various dimensions of the electrode members 33 are not critical and may be varied as desired.

The cup electrode 36 is hollow and comprises a generally cylindrical side wall 37 and a generally flat proximal end wall 38. The distal portion of the side 37 wall has an exterior surface 39 forming a ring electrode. The proximal portion of the side wall 37 is recessed. The stem 32 of the quad tip electrode 30 is received and secured within the hollow interior of the cup electrode 36, by polyurethane glue or the like which electrically insulates the composite tip electrode 30 from the cup electrode 36.

The quad tip electrode 30 comprises a central irrigation channel 40, formed for example by drilling, for receiving the distal end of the infusion tube 14. The central irrigation channel 40 extends axially from the proximal end of the quad tip electrode 30 to about the midpoint of the quad tip electrode 30. There, the channel 40 divides into four generally transverse branches 41, each branch extending distally and radially, e.g., at a 45° angle, through a separate electrode member 33. The diameters of the central channel 40 and branches 41 are not critical. A presently preferred composite tip electrode has a central irrigation channel 40 having a diameter of about 0.5 mm and four branches 41, each having a diameter of about 0.4 mm.

It is to be understood that the size and number of channels and/or branches may vary as desired. For example, each electrode member may have a plurality of branches rather than a single branch. Each branch may comprise secondary branches if desired. Rather than defined branches, the electrode members may be made of a porous material, e.g. as described in U.S. Pat. Nos. 5,643,197, and 5,462,521, which are incorporated herein by reference.

If desired, less than all of the electrode members may have irrigation branches or channels. For example, if only one or two of the electrode members 33 are intended for delivering RF energy during an ablation procedure, it may be desired that only those electrode members 33 comprise irrigation branches or channels.

The cup electrode 36 comprises a plurality of pass-through bores 54 for allowing insulated electrode lead wires 16 for each of the electrode members 33 of the quad tip electrode 30 to pass through the proximal end wall 38 of the cup electrode 36 when the electrode catheter is fully assembled. Each of the pass-through bores 54 are generally parallel to the axis of the catheter body 11, are aligned with an associated electrode lead bore 42, and are equally spaced about the proximal end of the cup electrode 36. To further insulate the cup electrode 36 from the quad tip electrode 30, each of the pass-through bores 54 has a meniscus insulator with a hole defined therethrough, as shown and described in U.S. Pat. No. 5,836,875 to Webster, Jr., which is incorporated herein by reference. The meniscus insulator precludes the electrical contact of the associated electrode lead wire 16 with the cup electrode 36.

In the embodiment shown, the cup electrode 36 further comprises an axial hole with a proximally extending cylindrical flange 51 around the hole. The distal portion of the infusion tube 14 extends through the flange 51 and axial hole and into the central irrigation channel 40 of the quad tip electrode 30 where it is fixedly secured by polyurethane glue or the like.

Figure 6:
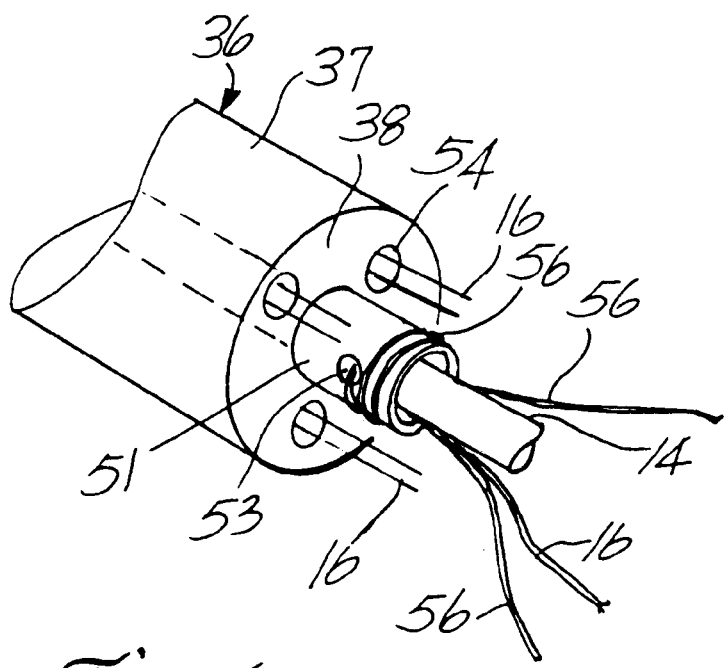
FIG. 6 is a cut-away perspective view of the proximal portion of the composite electrode of the catheter of FIG. 1 showing the connection of the electrode lead and safety wires.

The flange 51 has a transverse hole 53 at about its mid-point. An electrode lead wire 16 and a pair of safety wires 56 are fixedly attached to the stem 51 of the cup electrode 36. A preferred method of attaching the electrode lead wire 16 and safety wires 56 is shown in FIG. 6. The electrode lead wire 16 and safety wires 56 are inserted into the flange 51, passed out through the hole 53 and wrapped, preferably 1-½ times, around the flange 51. They are then soldered into place. The proximal end of the safety wires may be secured e.g. by polyurethane glue or the like anywhere in the tip section 12 proximal to the bridge tubing 22.

The cup electrode 36 can be of any suitable construction and is preferably made of platinum. The dimensions of the cup electrode are not critical. In a presently preferred embodiment, the length of the cup electrode 33 is about 0.13 inch, the depth of the cavity 50 about 0.08 inch, the outer diameter about 0.09 inch with a cavity diameter of about 0.08 inches.

The bridge tubing 22 is made of a short section of rigid tubular plastic, preferably PEEK (polyetheretherketone), and has an outer diameter about the same as flexible tubing 24 of the tip section 12 and an inner diameter about the same as the recessed proximal portion of the cup electrode 36 and the recessed distal potion of the flexible tubing 24. The bridge tubing 22 connects the split tip electrode 20 to the flexible tubing 24. At its distal end, the bridge tubing 22 receives the recessed proximal portion of the cup electrode 36 which is secured therein by polyurethane glue or the like. At its proximal end, the bridge tubing 22 receives the recessed distal end of the flexible tubing 24 which is also secured therein by polyurethane glue or the like.

The length of the bridge tubing 22 is selected to provide a gap within the interior of the bridge tubing 22 between the proximal end of the cup electrode 36 and the distal end of the flexible tubing 24. The gap is sufficiently long to allow space for the infusion tube 14 to bend or curve from the off-axis lumen 26 in the flexible tubing 24 into alignment with the axial hole and flange 51 in the cup electrode 33. The electrode lead wires 16 extend out of off-axis lumen 27 in the flexible tubing 24 to separate pass-through bores 54 in the cup electrode 36 and to the flange 51 of the cup electrode 33. A bridge tubing 22 having a length of about 6 to about 7 mm and providing a gap of about 1 to about 2 mm is presently preferred. It is understood that the bridge tubing may be made of any suitable,. generally rigid plastic which can withstand the temperature reached during an ablation procedure without significant, i.e., detrimental, deformation.

Figure 7:
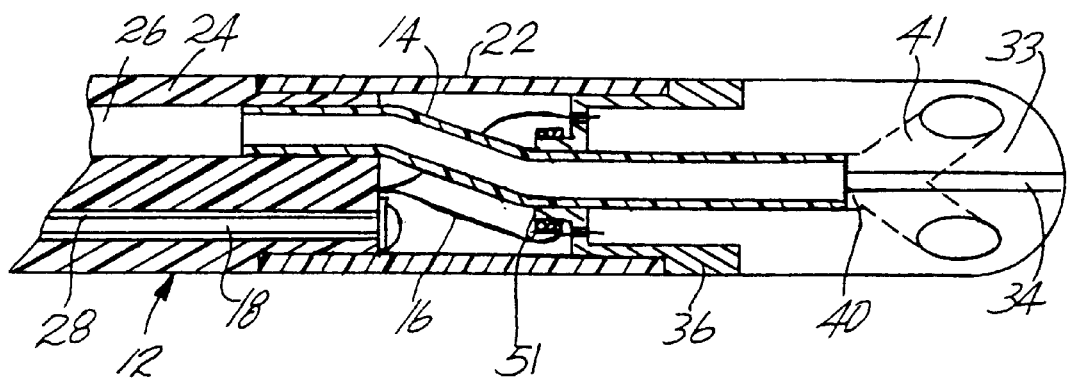
FIG. 7 is a longitudinal cross-sectional view of the catheter tip section of the embodiment of FIGS. 1 to 6 in which the infusion tube comprises two sections.

The infusion tube 14 may be made of any suitable material. Polyimide is presently preferred. It may be a single elongated tube which extends through the catheter body II through the first lumen 26 of the tip section 12, though the bridge tubing 22 and cup electrode 36 and into the irrigation channel 40 of the quad tip electrode. Alternatively, as shown in FIG. 7, the infusion tube 14 may comprise two sections, a proximal section which extends through the catheter body 11 and into the proximal end of the first lumen 26 of the tip section, the distal end of the proximal infusion tube section being secured in the first lumen 26 by polyurethane glue or the like. A second section of the infusion tube extends from the distal end of the first lumen 26 of the tip section 12, where it is secured by polyurethane glue or the like, through the bridge tubing 22 and flange 51 of the cup electrode 36 and into the central irrigation channel 40 of the quad tip electrode.

The proximal end of the infusion tube 14 extends out of a sealed opening in the side wall of the catheter body and terminates in a Luer hub or the like. Alternatively, the infusion tube 14 may extend through the control handle 13 and terminate in a luer hub or the like at a location proximal to the handle. In either such arrangement, fluids, e.g., saline, may be introduced into and passed through the infusion tube 14 and into and through the electrode members 33 of the composite tip 30 to cool the electrode members 33 during an ablation procedure. It is understood that other fluids, e.g., drugs, may also be passed through the infusion tube and out composite tip if desired. In a particularly preferred embodiment, the infusion tube is made out of thin walled polyamide tubing. It is understood that any suitable material may be used. Preferably having an outer diameter about the same as or slightly smaller than the diameter of the first lumen 26 of the tip section 12.

In a preferred embodiment, the electrode lead wires 16 associated with each electrode member 33 of the composite tip electrode 36 and cup electrode 36 is one wire of a pair of wires of dissimilar metals. The presently preferred wire pair is an enameled copper/constantan wire pair comprising a copper wire, having a thickness of about 0.003" and a constantan wire, having a thickness of about 0.003", enameled to the copper wire. Such an enameled wire pair is described in U.S. patent application Ser. No. 08/742,352 to Webster, Jr. which is incorporated herein by reference. In this configuration, the constantan wire, which has high strength supports the copper wire which is soft and fragile. Because the leads are constructed out of two different types of wire, the leads also serve as a thermocouple for measuring the temperature of the electrode. It is understood that any temperature monitoring means, e.g., a thermistor, a wire pair used exclusively as a thermocouple, may be used as desired. The leads 16 may also be used to interrupt power delivery in case of irrigation failure. The leads 16 extend into the electrode lead bores 42 of the electrode members 33 and are fixedly attached thereto by any suitable means, e.g., soldering or welding.

If desired, the irrigated split tip catheter of the present invention may comprise one or more ring electrodes 58 as shown, for example in FIG. 3. Attachment of electrode lead wires to such ring electrodes may be accomplished by any suitable means and/or procedure. A presently preferred procedure for attaching electrode leads to a ring electrode is described in U.S. Pat. No. 5,893,885 to Webster, Jr.

The puller wire 18 extends from the control handle 13 through the lumen 20 of the catheter body 11 and into the third off axis lumen 28 of the flexible tubing 24 of the tip section 12. The puller wire 18 is made of any suitable metal, such as stainless steel or Nitinol, and is preferably coated with Teflon® or the like. The coating imparts lubricity to the puller wire 18. The puller wire 18 preferably has a diameter ranging from about 0.006 to about 0.010 inches. The distal end of the puller wire 18 is anchored at or about the distal end of the flexible tubing 24 by any applicable means. A presently preferred means for anchoring the distal end of the puller wire is now described. Briefly, the puller wire 18 comprises a T-bar anchor which is fixedly attached to the distal end of the puller wire. The crossbar of the T-bar anchor lies outside of the distal end of the third off-axis lumen of the flexible tubing or in a notch created in the side wall of the flexible tubing which communicates with the third lumen. The size of the crossbar is selected so that it cannot be pulled into the third lumen. In this arrangement pulling on the puller wire results in deflection of the flexible tubing of the tip section in the direction of the third lumen. It is understood that the T-bar anchor may be secured in the notch in the side wall of the tip section tubing, if desired. Alternatively, the puller wire may be soldered or welded to the cup electrode.

To prevent deflection of the catheter body when the puller wire is pulled, there is provided a compression coil 17 in surrounding relation to the portion of the puller wire extending through the catheter body. The compression coil 17 extends from the proximal end of the catheter body 11 to the distal end of the catheter body 19 or the proximal end of the tip section 12. The compression coil 17 may be made from any suitable material, but is preferably made from stainless steel. The compression coil 17 is tightly wound on itself to provide flexibility, i.e., bending, but to resist compression. The inner diameter of the compression coil is slightly larger than the diameter of the puller wire. For example, when the puller wire 18 has a diameter of about 0.007 inches, the compression coil 17 preferably has an inner diameter of about 0.008 inches. The Teflon ® coating of the puller wire 18 allows it to slide freely within the compression coil 17. Along its length, the outer surface of the compression coil is covered by a flexible, nonconductive sheath to prevent contact between the compression coil 17 and any of the lead wires 16. A nonconductive sheath made of polyimide tubing is presently preferred. Such an arrangement involving a compression coil in surrounding relation to a puller wire is described in U.S. Pat. No. 5,935,124 which is incorporated fully herein by reference.

The compression coil 17 is preferably anchored at its proximal end to the proximal end of the stiffening tube in the catheter body 11 by a glue joint and at its distal end to the distal and of the catheter body 11 or the proximal end of the tip section 12, by another glue joint. Both glue joints are preferably comprised of polyurethane glue or the like.

Longitudinal movement of the puller wire is controlled by control handle 13. The control handle may be of any suitable design. A presently preferred control handle for a single puller wire is disclosed in U.S. Pat. No. Re 34,502 to Webster, Jr. which is incorporated herein by reference. Such a handle is particularly applicable if the proximal end of the infusion tube extends out of the catheter body terminating in a Luer hub or the like.

Figure 8:
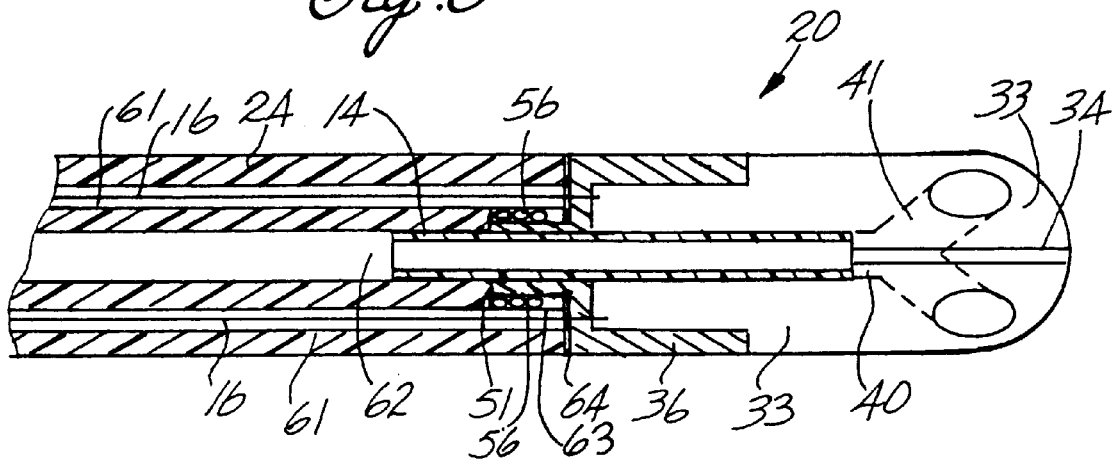
FIG. 8 is a longitudinal cross-sectional view of a tip section of a preferred embodiment of the invention which does not comprise a bridge tubing.

In another embodiment of the invention as shown in FIG. 8 and FIG. 8A, the tip section 12 comprises split tip electrode 20 which is attached directly to the flexible tubing 24. That is, there is no bridge tubing. In this embodiment, the split tip electrode 20 comprises a quad tip electrode as described above. The cup electrode 36 comprises a cylindrical side wall having an exterior surface forming a ring electrode. However, in this embodiment, there is no recessed proximal portion of the sidewall. That is, the entire sidewall of the cup electrode 36 forms a ring electrode.

The flexible tubing 24 comprises five lumens, 4 symmetrically spaced off-axis lumens 61 and an axial lumen 62. The flexible tubing 24 comprises an axial bore 63 at its distal end having a diameter slightly larger than the outer diameter of the cylindrical flange 51 of the cup electrode 36 to accommodate the safety wires 56 and cup electrode lead wire 16 which is wrapped around the outer circumference of the cylindrical flange 51. If desired, the distal ends of the safety wires 56 may be flattened to reduce the diameter of the trepanned hole 63 in the flexible tubing 24 needed to accommodate the cylindrical flange 51 and safety wires 56 wrapped thereabout.

The infusion tube 14 extends through the axial lumen 62 of the flexible tubing 24, through the flange 51 of the cup electrode 36 and directly into the central irrigation channel 40 of the quad tip electrode. As described above, the infusion tube may be a single elongated tube or may comprise discrete proximal and distal sections.

The electrode lead wires 16, preferably enameled wire pairs as described above, for the electrode members 33 of the quad tip electrode extends through one (or more) of the off-axis lumens 62. A small gap 64 is provided between the distal end of the flexible tubing 24 and the proximal end plate of the cup electrode 36. Within this gap 64, the electrode lead wires 16 which are not aligned with a pass through bore in the cup electrode 36 may pass from the off-axis lumen(s) 61 to pass through bores 54 of the cup electrode 36 and then into the electrode lead bores 42 of the electrode members 33 of the quad tip electrode 30 where they are fixedly attached.

In this embodiment, there are two puller wires 18 which extend through the catheter body 11 and into diametrically opposed off-axis lumens 61 in the flexible tubing 24. The distal ends of the puller wires 18 preferably comprise T-bar anchors 65 as described above and are preferably anchored by glue 66 in notches 67 in the side wall of the flexible tubing 24 as shown in FIG. 8A. Alternatively, the distal ends of the puller wires may be soldered or welded directly to the proximal end plate of the cup electrode 36.

The cup electrode 36 is fixedly secured to the distal end of the flexible tubing 24 by polyurethane glue or the like which fills the gap 64.

Figure 9:
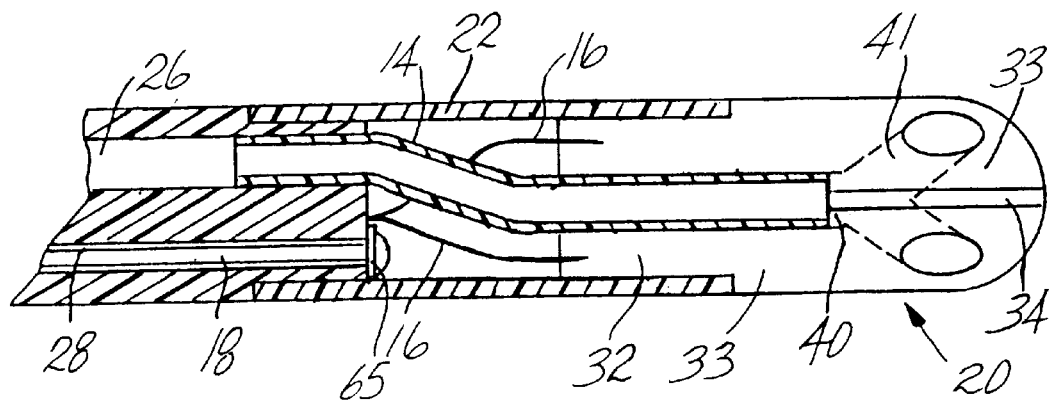
FIG. 9 is a longitudinal cross-sectional view of the tip section of a preferred embodiment of the invention in which the split tip electrode does not include a cup electrode.

In yet another embodiment of the invention shown in FIG. 9, the tip section comprises a section of flexible tubing 24, a bridge tubing 22 and the split tip electrode 20 comprises a quad tip electrode, but no cup electrode. In such an embodiment, the recessed stem 32 of the quad tip electrode extends directly into the distal end of the bridge tubing 22 and is secured therein by polyurethane glue or the like.

At its proximal end, the bridge tubing 22 receives the recessed distal end of the flexible tubing 24. The flexible tubing 24 preferably comprises three off-axis lumens, as described with respect to the embodiment of FIGS. 1–7, through which an infusion tube 14, electrode lead wires 16 and a puller wire 18 extend. It is understood that, if desired, three lumen flexible tubing 24 may be used in which all lumens are diametrically aligned. A three off-axis lumen is preferred, however, because it provides superior strength. If bidirectional capability is desired, the flexible tubing preferably comprises four off-axis lumens, and the puller wires 18 extending through diametrically opposed off-axis lumens.

Figure 10:
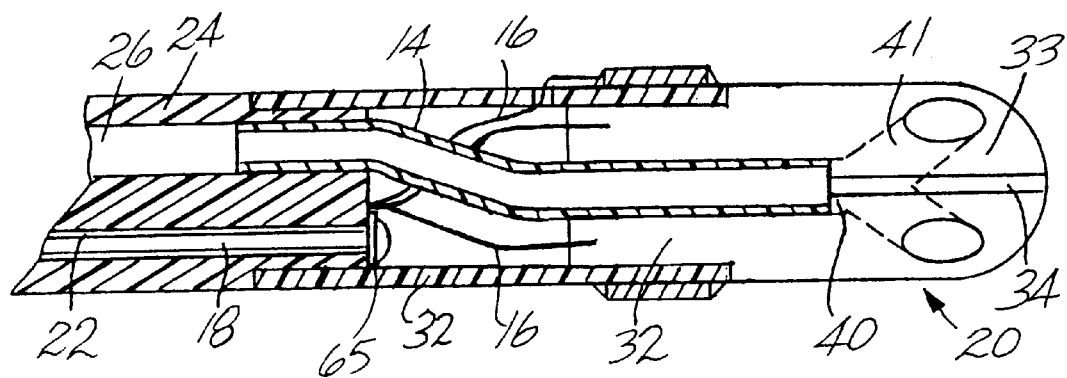
FIG. 10 is a longitudinal cross-sectional view of the tip section of another embodiment of the invention similar to FIG. 9, in which the split tip electrode includes a ring electrode.

If desired, an electrically isolated ring electrode 58 may be mounted around the distal end of the bridge tubing 22 as shown in FIG. 10. In such an embodiment, the lead wire for the ring electrode extends through a small hole in the bridge tubing 22 and across the exterior surface of the bridge tubing to the electrode 58. The lead wire is covered and the hole in the bridge tubing is filled with polyurethane resin or the like. More than one ring electrode may be carried by the bridge tubing or the flexible tubing.

Figure 11:
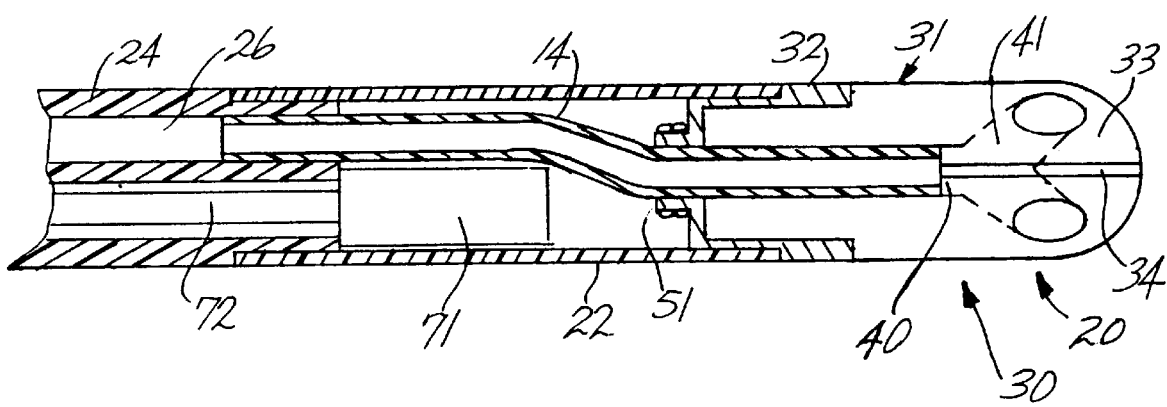
FIG. 11 is a longitudinal cross-sectional view of the tip section of another preferred embodiment of the invention including an electromagnetic sensor.

In a further embodiment of the invention as shown in FIG. 11, the tip section 12 carries an electromagnetic sensor 71 within the bridge tubing 22. In this embodiment, the split tip electrode 20 may (as shown) or may not comprise a cup electrode 36, as desired. The flexible tubing 24 comprises at least three off-axis lumens, one for a cable 72 which extends from the electromagnetic sensor 71 through the tip section 12, catheter body 11 and handle 13 to a connector for connection to a signal processing and imaging means. If desired, a circuit board can be provided in the control handle. The sensor cable is connected to the circuit board, which amplifies the signal received from the electromagnetic sensor and transmits it to a computer in a form understandable by the computer. The other two lumens in the flexible tubing are for the infusion tube 14 and electrode lead wires (not shown) and for a puller wire (not shown). Again, if bidirectional capability is desired, a fourth off-axis lumen in the flexible tubing would be required for the second puller wire. Suitable electromagnetic sensors and signal processing and imaging means are commercially available from Cordis Webster, Inc., and are described in U.S. Pat. Nos. 5,558,091, 5,443,489, 5,480,422, 5,546,951, 5,568, 809, and 5,391,199 and International Publication No. W095/ 02995 which are incorporated herein by reference.

In this embodiment, the bridge tubing 22 is sufficiently long to allow the infusion tube 14 to curve around the electromagnetic sensor 71 and into the axial flange 51 of the cup electrode 36 into the central irrigation channel 40 in the quad tip electrode.

It is to be understood that, with respect to the embodiments described above comprising a single puller wire, the catheter may comprise two or more puller wires. Likewise, those embodiments described above comprising a pair of puller wires may, if desired, comprise only a single puller wire. In an embodiment comprising a pair of puller wires, the flexible tubing 24 of the tip section 12 would preferably comprise four off-axis lumens. The puller wires would preferably extend into diametrically opposed off axis lumens and be anchored at the distal end of the flexible tubing as described above. Control handles for manipulating a pair of puller wires are well known. Preferred control handles are described in U.S. Pat. Nos. Re 34,502, 6,123,699, and 6,120,476 to Webster, Jr., and U.S. patent application Ser. No. 09/130,359 to Ponzi, all of which are incorporated herein by reference.

In the event that an omni-directional capability is desired, the catheter may comprise three or more, and preferably four puller wires. In such an embodiment, the flexible tubing of the tip section would preferably comprise four off-axis lumens, one in each quadrant, through which the puller wires extend. A central lumen in the tip section would preferably be provided to accommodate the infusion tube and electrode lead wires. Such an arrangement of lumens and puller wires and a control handle for manipulating the puller wires is disclosed in U.S. Pat. No. 6,123,699 to Webster, Jr., which is incorporated herein by reference.

It is to be understood that any suitable means for controllably deflecting the tip section in one or more may be used. Examples of other such means can be found in U.S. Pat. Nos. 5,656,030 to Hunjan, et al, 5,195,968, 5,254,088, 5336,189, 5,531,686 to Lundquist, et al, 5,273,535, 5,281, 217, 5,370,678 to Edwards, et al, 5,358,478 to Thompson, et al, 5,364,351 and 5,456,664 to Hemzelman, all of which are incorporated herein by reference.

It is understood that any construction providing a split tip electrode comprising two or more electrode members may be used in this invention. The presence of a cup electrode, while preferred is not required. Likewise, the presence of a bridge tubing is preferred, but not required.

The ablation system comprises a first RF generator for generating a low level RF impedance current and a second RF generator for generating an RF ablation current.

The low level RF impedance current may be any current having a power level and frequency which allows detection of impedance without ablating the tissue or creating fibrillation, i.e., resulting in muscle capture, and preferably is at a frequency that tends to maximize the difference in impedance of tissue as compared with blood pool. A current of 2 microamperes at 50 KHz is presently preferred.

The RF ablation current may be any current of sufficient power and frequency to ablate myocardial tissue. An ablation current of from about 0.25 to about 1.0 amperes or more, preferably about 0.5 to 0.75 amperes, at a frequency of from about 400 to about 700 KHz. and preferably about 500 KHz. Higher power levels which result in deeper tissue lesions are preferred as long as charring of the tissue surface can be avoided, e.g., by irrigation, and steam pops can be avoided.

The first and second RF generators may be two separate devices or, as shown in FIG. 1, may be combined into a single device. A presently preferred RF generator is the Stockert EP/Shuttle RF generator which is commercially available from Cordis Webster, Inc. This generator includes means for generating a low level RF impedance current and an RF ablation current. This RF generator also comprises means for receiving impedance signals associated with each of the electrodes and filters for separating these signals from the RF ablation currents in order to obtain clear impedance signals which may be recorded and/or displayed. This generator comprises displays for displaying the temperature and impedance associated with an electrode member and a switch for selectively switching each of the displays from one electrode member to another. The Stockert RF generator also comprises a display for showing the amount of time which has elapsed during which RF current is delivered to the ablating electrode member(s). It also has a safety shut-off which shuts off the RF ablation current if the temperature or impedance reaches a select predetermined level.

The monitor/display may comprise one or more suitable devices for receiving signals indicative of the electrical activity of the heart, temperature of the electrode members and/or impedance associated with each of the electrode members and for generating a display and/or record of the received signals. As noted above, a display/monitor for displaying and/or recording the electrode member temperature and impedance may be incorporated into the RF generator.

Alternatively, it may be built into the signal processor (discussed below). Independent stand alone displays may be used as desired. Suitable display/monitors for receiving and displaying electrical signals received from a pair of electrode members as a bipolar electrogram are commercially available, e.g., from Prucka Engineering. The metering pump may be any suitable metering pump capable of metering an amount of from about 5 to about 60 cc/min., and preferably from about 20 to about 40 cc/min., of a cooling fluid, e.g., a saline solution, into and through the infusion tube of the irrigated tip electrode catheter. The Mark V Plus injection pump commercially available from Medrad, Inc., or the Model 7100 volumetric infusion pump available from IVAC Medical Systems are examples of suitable metering pumps for use in the present invention.

The signal processor may be any programmable microprocessor or the like. The signal processor is electrically connected to the RF generator(s), the monitor/display and the pump, as well as the split tip catheter and the reference electrodes. In a preferred embodiment, the signal processor is programmed to activate the RF generator to generate a low level RF impedance current, e.g., about 2 microamps at about 50 KHz, and to transmit such current to each of the electrode members of the split tip electrode. The signal processor then receives signals indicative of the impedance associated with each electrode member, compares those impedance signals and determines which electrode members are associated with the highest impedances. The signal processor then automatically activates the RF generator to generate an RF ablation current and to transmit that current only to those electrode members determined to be in best contact with the myocardium.

During ablation, irrigation is used to keep the ablating electrode members cool. It also reduces the temperature of the tissue at the tissue-electrode interface. This allows for higher RF current to be used resulting in deeper heating, i.e., the maximum tissue temperature would be below the surface rather than at the surface, and a larger lesion. Irrigation, however, causes the temperature of the electrode to be significantly less than that of the tissue at the tissue-electrode interface. For this reason, it is preferred to use intermittent irrigation so that, during the periods of no irrigation, the temperature of the electrode members in contact with the tissue will rise and better approximate the tissue surface tissue temperature. During the periods when irrigation is stopped, it is preferred to also cease the transmission of RF ablation current.

Accordingly, during the ablation procedure, the signal processor activates the pump to pump saline solution or other cooling fluid through the catheter to cool the ablating electrode members. Preferably, the signal processor is programmed to activate the pump and RF generator intermittently, i.e., to activate the pump and RF generator for a select period of time, preferably from about 1 to about 10 seconds and more preferably about 5 seconds, and then deactivate the pump and RF generator for another period of time, preferably from about 1 to about 10 seconds, more preferably about 5 seconds and to continuously repeat this cycle.

During ablation the signal processor receives signals from the thermocouple or thermistor associated with each of the electrode members, the signals being indications of the temperatures of the electrode members, particularly at the end of a cycle wherein the irrigation and RF ablation current are shut off. These temperature signals are used to provide an estimate of the temperature of the tissue at the tissue electrode member interface. The signal processor is programmed to reduce or terminate the transmission of RF ablation current when the temperature of an ablating electrode member reaches a predetermined level, e.g., 90° C.

During the ablation process, the signal processor preferably activates the RF generator to continue to transmit low level RF current signals to each of the electrode members and receives signals indicating the impedance through the blood and/or tissue during the ablation procedure associated with each such electrode member. The signal processing unit determines the difference in impedance signals associated with those electrode members in contact with the myocardium and those in contact only with the blood pool. As the tissue heats up during the ablation procedure, the impedance through the tissue decreases whereas the impedance through the blood pool generally remains the same. The difference in impedance through the tissue as compared to through the blood, provides an indication of the maximum temperature of the tissue. The signal processor is therefore programmed to reduce or terminate the RF current being delivered to the selected electrode members when the impedance associated with those electrode members drops to a predetermined level or when the difference between the impedance associated with the ablating electrode members in contact with the myocardium and the impedance associated with the electrode members in contact only with the blood pool reaches a predetermined level.

For a given set of parameters, e.g., power level, frequency, amount of irrigation, cycling periods. angle of the ablation electrode, etc., the correlation between temperature and impedance may be determined, for example, by in vivo testing on dogs. A preferred test comprises a series of ablations under controlled conditions using, e.g., dog thigh muscle. The temperature of the muscle at various depths can be measured using a fluoroptic thermal probe, e.g., Luxtron model 3000 or the like, and correlated against measured impedance. A testing procedure suitable for use in the present invention is described in "Comparison of In Vivo Tissue Temperature Profile and Lesion Geometry for Radiofrequency Ablation With a Saline-Irrigated Electrode Versus Temperature Control in a Canine Thigh Muscle Preparation" Circulation, 1995; 91:2264–2273, and Inverse Relationship Between Electrode Size and Lesion Size During Radiofrequency Ablation With Active Electrode Cooling, Circulation, 1998; 98:458–465, which are incorporated herein by reference. From such testing, a correlation between measured impedance, and maximum tissue temperature can be obtained. The signal processor is programmed to reduce or shut down the transmission of RF ablation current to the electrodes if the maximum tissue temperature of the tissue exceeds a predetermined level, e.g., 90° C., as determined by the impedance measurements.

It is understood that information regarding the tissue temperature can be obtained by measuring the impedance associated with only those electrode members being used for ablation. However, monitoring the impedance associated with each ablating electrode member, i.e., those in contact with the myocardium and those non-ablating electrode members in contact with only the blood pool, is preferred. In such a system, changes in impedance due to factors other than the increasing tissue temperature would not affect, or at least would have minimal effect, on the impedance-temperature correlation.

Monitoring the impedance associated with each of the electrode members during ablation also allows the electrophysiologist to continue to monitor which electrode members are in contact with the myocardium and hence, whether the catheter tip has rolled or rotated during ablation.

It is understood that the signal processor need not accomplish all of the functions described above. Indeed, many, if not all, of the functions described above with respect to the signal processor may be accomplished manually, e.g., by the electrocardiologist. For example, the electrocardiologist may analyze the various impedance measurements described above and then manually select, e.g., by a dial on the RF generator, the electrode members in best contact with the myocardium to receive RF ablation current. The electrocardiologist may then manually activate the RF generator to generate that RF ablation current. Likewise, the electrocardiologist may monitor temperature and impedance readings during ablation and manually reduce or discontinue RF current if the temperature and/or impedance readings indicate excessive tissue temperature.

In use, the split tip electrode catheter is inserted into the heart and the split tip electrode is contacted with heart tissue at various locations in the heart to map the electrical activity of the heart. At each such location, electrode members in contact with the myocardium sense electrical signals propagating through the heart. By means of the electrode arrangement of the split tip electrode at least two electrodes will be in contact with the myocardium. If the tip is lying parallel to the tissue or at an angle of less than about 30° to about 45°, the ring electrode is also in contact with or close to the myocardium. This enables two orthogonal electrical signals, each with a voltage level and polarity, to be sensed, which provides sufficient data to determine excitation wave front direction. If the split tip electrode is oriented perpendicular to the endocardial surface, all four of the hemispherical electrode members of the split tip electrode would be in contact with the myocardium. In this orientation, at least two orthogonal electrograms can be obtained from the four hemispherical electrode members. This also provides sufficient data to determine a wave front direction.

Once the endocardium is sufficiently mapped to determine the location to be ablated, the electrode members of the split tip electrode in good contact with the endocardial tissue are determined. This is done by delivering a low level RF current, e.g., about 2 microamperes at about 50 KHz, to each electrode member of the split tip electrode. The impedance between each such member and a reference electrode(s) such as a skin patch electrode(s) on the patient is then measured. The impedance associated with those electrode members in contact with the tissue will be higher than those that are surrounded by the blood pool. Accordingly, the electrode member(s) with the highest impedance will be the one(s) in best contact with the endocardial tissue.

Once the ablation site has been located and the electrode members most fully in contact with the endocardial tissue have been identified, RF current for ablation is selectively delivered to those electrode members. RF energy is delivered at a power level and at a frequency and for a time sufficient to kill enough heart tissue to interrupt the aberrant electrical pathway. A time generally in the range of from about 30 seconds to about 2 minutes is typical.

During ablation, it is important to prevent charring of the surface of the myocardium and overheating of the deep heart tissue which could result in "steam pops." Accordingly, temperature of the tissue is preferably monitored in two ways. First, each electrode member of the split tip electrode has a temperature sensor, e.g., a thermocouple or thermistor, associated with it. The temperature of the endocardium at the interface with the electrode, is estimated by monitoring the temperature of the electrode members in contact with the endocardium. Preferably, the electrode members are irrigated during ablation. This allows the temperature of the electrode members to be controlled so that a greater amount of RF current can be delivered through the electrode members without excessive temperature rise. Irrigation, however, creates a greater differential between electrode temperature and tissue interface temperature. As a result, irrigation and the delivery of RF ablation current is preferably intermittent, with periods of irrigation and RF ablation current separated by periods of no irrigation and no ablation current. During the latter periods, the temperature of the electrode members in contact with the tissue will rise to a temperature more indicative of the tissue interface temperature.

As a result of the greater RF current which can be used with an irrigated ablation electrode, the tissue below the interface, which tends to heat more slowly, will rise to a temperature greater than that at the interface. This temperature is estimated by monitoring the impedance associated with each of the electrode members. As the tissue heats, the tissue impedance decreases whereas the impedance of the blood pool remains essentially constant. Hence, by monitoring the impedance associated with the electrode members in contact with the tissue and comparing the decrease in that impedance to the impedance associated with non-tissue contacting electrode members and correlating that impedance difference with temperature (as described above), the maximum tissue temperature can be estimated and excessive rise in tissue temperature can be avoided.

If desired, the split tip electrode catheter may be equipped with an electromagnetic sensor positioned proximal to the split tip electrode. The electromagnetic sensor in combination with suitable signal processing and imaging means, as described above, allow for the generation of a three-dimensional image of the interior contours of the heart chamber in which the distal tip of the catheter is located and to monitor the location of the split tip electrode within that heart chamber.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Accordingly, the foregoing description should not be read as pertaining only to the precise structures described and illustrated in the accompanying drawings, but rather should be read consistent with and as support to the following claims which are to have their fullest and fair scope.

What is claimed is:

1. A system for ablating tissue and estimating the maximum sub-surface temperature of said tissue comprising:
    a split tip electrode catheter comprising:
        an elongated catheter body having a proximal and distal end and at least one lumen extending therethrough;
        a catheter tip section at the distal end of the catheter body comprising a section of flexible tubing having proximal and distal ends and at least one lumen therethrough, the proximal end of the flexible tubing being fixedly attached to the distal end of the catheter body, said catheter tip section further comprising a split tip electrode which comprises at least two electrically isolated electrode members fixedly attached to the distal end of the flexible tubing, each electrode member comprising at least one irrigation passage;
    at least one indifferent electrode attachable to the exterior of a patient;
    means for generating a low level RF impedance current and for transmitting said impedance current to each electrode member of the split tip electrode;
    means for generating an RF ablation current and for transmitting said ablation current to each electrode member of the split tip electrode;
    means for electrically connecting each electrode member of the split tip electrode to the low level RF impedance current generating means and the RF ablation current generating means;
    means for receiving electrical signals indicative of the impedance between each electrode member and the at least one indifferent electrode during the transmission of RF ablation current and for separating such impedance indicating signals from other received signals; and
    a programmable signal processor, electrically connected to the RF impedance current generating means, the RF ablation current generating means, each of the electrode members of the split tip electrode, the at least one indifferent electrode and the signal receiving means, said signal processor being programmed to simultaneously activate the RF impedance current generating means and the RF ablation current generating means to transmit RF impedance current and RF ablation current and to estimate the maximum subsurface temperature based on the received electrical impedance-indicating signals.

2. A system as claimed in claim 1 wherein the signal processor is further programmed to deactivate the RF ablation current generating means if the estimated maximum subsurface temperature reaches a predetermined temperature.

3. A system as claimed in claim 1 further comprising means for controllably deflecting the tip section in at least one direction.

4. A system as claimed in claim 1 wherein the split tip electrode comprises four electrode members.

5. A system as claimed in claim 4 wherein the four electrode members are generally the same and are arranged symmetrically around a longitudinal axis of the tip section.

6. A system as claimed in claim 5 further comprising a ring electrode adjacent proximally to the four electrode members.

7. A system as claimed in claim 1 wherein the low level RF impedance current has ampere level and frequency that allows detection of impedance without ablating tissue in contact with the split tip electrode and without creating fibrillation of a patient's heart.

8. A system as claimed in claim 7 wherein the ampere level and frequency selected are ones with which there is a measurable difference in impedance of tissue as compared to the blood pool.

9. A system as claimed in claim 1 wherein the RF impedance current is about 2 microamperes at about 50 KHz.

10. A system as claimed in claim 1 wherein each of said at least two electrode members of the split tip electrode comprises at least one irrigation passage and wherein the system further comprises a metering pump for pumping a cooling fluid through the catheter and the at least one irrigation passage in each electrode member to cool the electrode members during ablation.

11. A system as claimed in claim 10 wherein the signal processor is further programmed to activate the pump to pump cooling fluid through the catheter to cool the electrode members while an RF ablation current is being transmitted to one or more electrode members.

12. A system for ablating tissue and estimating the surface and maximum subsurface temperature of said tissue comprising:
    a split tip electrode catheter comprising:
        an elongated catheter body having a proximal and distal end and at least one lumen extending therethrough;

a catheter tip section at the distal end of the catheter body comprising a section of flexible tubing having proximal and distal ends and at least one lumen therethrough, the proximal end of the flexible tubing being fixedly attached to the distal end of the catheter body, said catheter tip section further comprising a split tip electrode which comprises at least two electrically isolated electrode members fixedly attached to the distal end of the flexible tubing each electrode member comprising at least one irrigation passage;

at least one indifferent electrode attachable to the exterior of a patient;

means for generating a low level RF impedance current and for transmitting said impedance current to each electrode member of the split tip electrode;

means for generating an RF ablation current and for transmitting said ablation current to each electrode member of the split tip electrode;

means for electrically connecting each electrode member of the split tip electrode to the low level RF impedance current generating means and the RF ablation current generating means;

means, including a pump, for infusing a cooling fluid through the catheter and each of the electrode members to cool the electrode members during ablation;

temperature sensing means, attached to each electrode member of the split tip electrode, for generating a signal indicative of the temperature of the electrode member to which it is attached;

means for receiving electrical signals indicative of the impedance between each electrode member and the at least one indifferent electrode during the transmission of RF ablation current and for separating such impedance indicating signals from other signals received; and signal processing means, electrically connected to the RF impedance current generating means, the RF ablation current generating means, the pump of the infusing means, each of the electrode members of the split tip electrode, the at least one indifferent electrode, the temperature sensing means and the signal receiving means, for activating the RF impedance generating means to transmit an impedance current to each of the electrode members of the split tip electrode, for receiving electrical signals indicative of the impedance between each of the electrode members of the split tip electrode and the at least one indifferent electrode and for identifying the electrode member(s) associated with the highest impedance signal(s) received as the electrode member(s) in contact with tissue, and thereafter for intermittently activating the pump of the infusing means and the RF ablation current generating means so that there are ON periods wherein cooling fluid is delivered to the electrode members and RF ablation current is transmitted to the identified tissue-contacting electrode members and OFF periods wherein no cooling fluid is delivered to the electrode members and no RF ablation energy is transmitted to the identified tissue-contacting electrode members for estimating the surface temperature of tissue in contact with the electrode members from the signals received from the temperature sensing means during the OFF periods, for activating the RF impedance current generating means to transmit impedance current to the electrode members of the split tip electrode during at least the ON periods and for estimating the maximum subsurface temperature of tissue heated by the RF ablation current from the received impedance-indicating signals.

13. A system as claimed in claim 12 further comprising means for controllably deflecting the tip section in at least one direction.

14. A system as claimed in claim 12 wherein the split tip electrode comprises four electrode members.

15. A system as claimed in claim 14 wherein the four electrode members are generally the same and are arranged symmetrically around a longitudinal axis of the tip section.

16. A system as claimed in claim 15 further comprising a ring electrode adjacent proximally to the four electrode members.

17. A system as claimed in claim 12 wherein the low level RF impedance current has ampere level and frequency that allows detection of impedance without ablating tissue in contact with the split tip electrode and without creating fibrillation of a patient's heart.

18. A system as claimed in claim 17 wherein the ampere level and frequency selected are ones with which there is a measurable difference in impedance of tissue as compared to the blood pool.

19. A system as claimed in claim 18 wherein the RF impedance current is about 2 microamperes at about 50 KHz.

20. A system as claimed in claim 12 wherein the signal processing means is further programmed to deactivate the RF ablation current generating means if the estimated maximum subsurface temperature reaches a predetermined temperature.

21. A method for ablating tissue and for estimating the increase in subsurface temperature of tissue at an ablation site during an ablation procedure comprising:

providing a split tip electrode catheter comprising:
an elongated catheter body having a proximal and distal end and at least one lumen extending therethrough;
a catheter tip section at the distal end of the catheter body comprising a section of flexible tubing having proximal and distal ends and at least one lumen therethrough, the proximal end of the flexible tubing being fixedly attached to the distal end of the catheter body, said catheter tip section further comprising a split tip electrode which comprises at least two electrically isolated electrode members fixedly attached to the distal end of the flexible tubing;

introducing the catheter into a lumen in the body of a patient and positioning the catheter so that at least one electrode member of the split tip electrode is in contact with the tissue to be ablated and at least one other electrode member of the split tip electrode is only in contact with the blood pool;

positioning at least one indifferent electrode on the patient;

transmitting an RF ablation current to at least one tissue-contacting electrode member of the split tip electrode;

transmitting a low level RF impedance current through the at least one tissue contacting electrode member of the split tip electrode during transmission of RF ablation current to the at least one tissue-contacting electrode member;

monitoring the impedance between the at least one tissue-contacting electrode member and the at least one indifferent electrode and the impedance between the at least one non-tissue-contacting electrode member and the indifferent electrode; and estimating the increase in subsurface tissue temperature from the change in the difference between the impedance associated with the at least one tissue-contacting electrode member and the impedance associated with the at least one non-tissue-contacting electrode member.

22. A method as claimed in claim 21 further comprising reducing or terminating the transmission of RF ablation current to the at least one tissue-contacting electrode member of the split tip electrode when the change in measured impedance reaches a predetermined level which indicates that a predetermined maximum subsurface temperature has been reached.

23. A method as claimed in claim 21 wherein the catheter further comprises means for controllably deflecting the tip section in at least one direction.

24. A method as claimed in claim 21 wherein the tip electrode further comprises four electrically isolated electrode members.

25. A method as claimed in claim 24 wherein the four electrode members are generally the same and are arranged symmetrically around a longitudinal axis of the tip section.

26. A method as claimed in claim 25 wherein the catheter further comprises a ring electrode adjacent proximally to the four electrically isolated electrode members.

27. A method as claimed in claim 21 wherein the low level RF impedance current has ampere level and frequency that allows detection of impedance without ablating tissue in contact with the tip electrode and without creating fibrillation of a patient's heart.

28. A method as claimed in claim 27 wherein the ampere level and frequency selected are ones with which there is a measurable difference in impedance of tissue as compared to the blood pool.

29. A method as claimed in claim 28 wherein the RF impedance current is about 2 microamperes at about 50 KHz.

30. A method as claimed in claim 21 wherein the tip electrode comprises at least one irrigation passage and wherein cooling fluid is passed through the catheter and the least one irrigation passage to cool the tip electrode while an RF ablation current is being transmitted to the tip electrode.

* * * * *

UNITED STATES PATENT AND TRADEMARK OFFICE
CERTIFICATE OF CORRECTION

PATENT NO. : 6,217,574 B1
DATED : April 17, 2001
INVENTOR(S) : Wilton W. Webster, Jr.

It is certified that error appears in the above-identified patent and that said Letters Patent is hereby corrected as shown below:

<u>Title page,</u>
Item [75], Inventor, the Inventor's name should read -- Wilton W. Webster, Jr. --.
Item [62], Related U.S. Application Data, should read:
 -- Division of application No. 09/205,628,
 filed on Dec. 3, 1998. --.
Item [56], References Cited, U.S. PATENT DOCUMENTS replace:
 "4,960,134 10/1990 WEbster, Jr..128/786" with
 -- 4,960,134 10/1990 Webster, Jr..128/786 --.

<u>Column 16,</u>
Line 49, replace "KHz" with -- kHz --.

<u>Column 18,</u>
Line 24, replace "KHz" with -- kHz --.

<u>Column 20,</u>
Line 14, replace "KHz" with -- kHz --.
Line 18, before "least" insert -- at --.

Signed and Sealed this

Eleventh Day of June, 2002

*Attest:*

JAMES E. ROGAN
*Attesting Officer*     *Director of the United States Patent and Trademark Office*